(12) United States Patent
Doerr et al.

(10) Patent No.: US 8,532,767 B2
(45) Date of Patent: Sep. 10, 2013

(54) DEVICE FOR MEDICAL APPLICATIONS AND ELECTROMEDICAL IMPLANT

(75) Inventors: Thomas Doerr, Berlin (DE); Ingo Weiss, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 0 days.

(21) Appl. No.: 13/452,905

(22) Filed: Apr. 22, 2012

(65) Prior Publication Data

US 2012/0290029 A1 Nov. 15, 2012

Related U.S. Application Data

(60) Provisional application No. 61/484,242, filed on May 10, 2011.

(51) Int. Cl.
*A61N 1/00* (2006.01)

(52) U.S. Cl.
USPC .......................................................... 607/11

(58) Field of Classification Search
USPC ............................................... 607/11, 9, 116
See application file for complete search history.

(56) References Cited

U.S. PATENT DOCUMENTS

| | | | |
|---|---|---|---|
| 5,531,766 | A | 7/1996 | Kroll et al. |
| 2005/0197677 | A1 | 9/2005 | Stevenson |
| 2007/0112398 | A1 | 5/2007 | Stevenson et al. |
| 2009/0105789 | A1 | 4/2009 | Olsen |
| 2010/0174348 | A1 | 7/2010 | Bulkes et al. |
| 2011/0137390 | A1* | 6/2011 | Hill .............................. 607/116 |

OTHER PUBLICATIONS

European Search Report dated Sep. 7, 2012, 5 pages.

* cited by examiner

*Primary Examiner* — Robert N Wieland
(74) *Attorney, Agent, or Firm* — Arc IP Law, PC; Joseph J. Mayo

(57) ABSTRACT

A device for medical applications, comprising an elongated conductive element having one proximal end and one distal end, wherein the latter undergoes a temperature increase by absorbing energy from an electromagnetic field, comprising a separating element disposed in the elongated conductive element for the galvanic separation of the proximal end from the distal end.

16 Claims, 9 Drawing Sheets

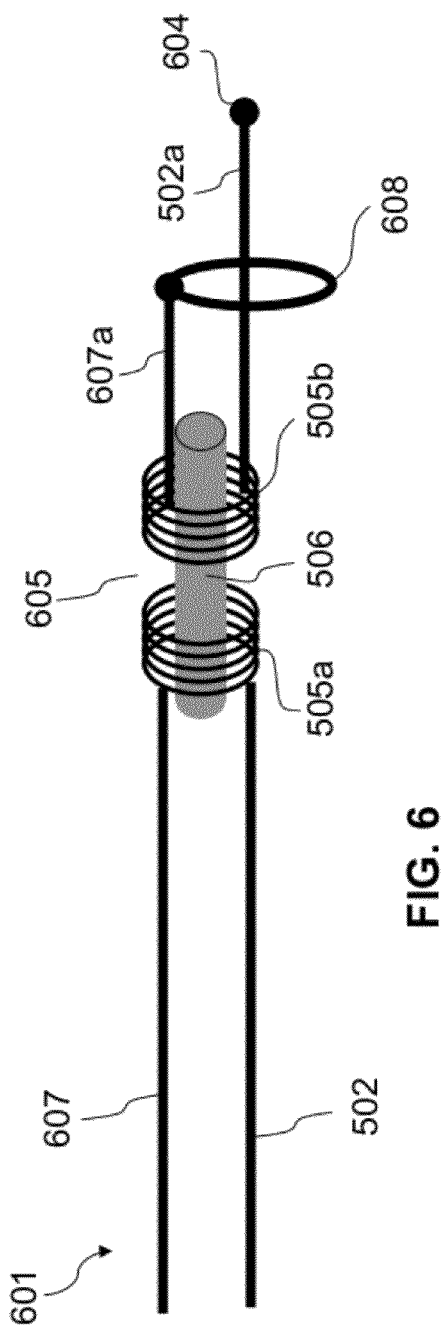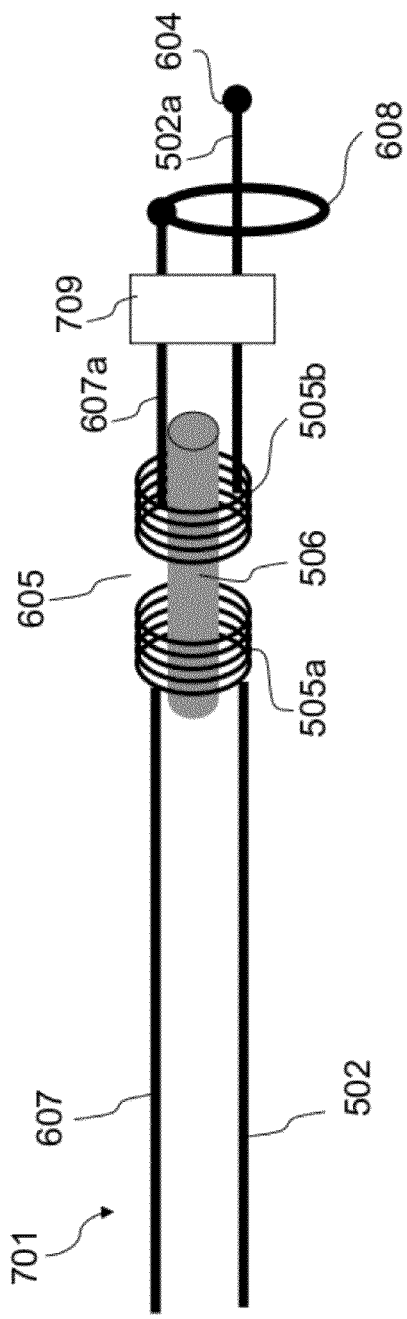
FIG. 6
FIG. 7A

DEVICE FOR MEDICAL APPLICATIONS AND ELECTROMEDICAL IMPLANT

This application claims the benefit of U.S. Provisional Patent Application 61/484,242, filed on 10 May 2011, the specification of which is hereby incorporated herein by reference.

BACKGROUND OF THE INVENTION

1. Field of the Invention

At least one embodiment of the invention relates to a device for medical applications, which comprises an elongated, conductive element having a distal end. Such an elongated, conductive element can be an electrode lead, for example.

2. Description of the Related Art

Such devices are used e.g. in an implantable defibrillation arrangement 100 of the type known e.g. from U.S. Pat. No. 5,531,766 and illustrated in FIG. 1. In order to stimulate the heart H of the patient P, a defibrillator 110 is electrically connected to a lead 101 which, in this case, comprises a special electrode in the form of a shock electrode 104 disposed on the distal end thereof and which is placed in the patient's heart. Defibrillation typically takes place in a monopolar manner via a current path between electrode 104 and an electrode (not shown), which is disposed more or less further away from the heart H to be stimulated. For example, the housing of defibrillator 110, which contains the units for the detection of cardiac signals and for generating electrical impulses, can function as counter-electrode.

FIG. 2 shows the distal end of another lead 201. The tip of the lead comprises two electrodes 204 and 208 for performing a so-called bipolar cardioversion. While electrode 204 forms a contact at the tip of lead 201, electrode 208 is designed as an annular contact on the circumference of the lead. The supply lead comprises two spiral-wound leads 202 and 207, which electrically connect electrodes 204 and 208 to a connecting plug (not shown) on the proximal end of the lead.

At this time, patients who have a conventional defibrillation arrangement according to FIG. 1 cannot be examined using a magnetic resonance tomograph (MRT) or an MRI scanner, since the strong electromagnetic alternating fields can induce intense heating of the lead tip and thereby damage the surrounding tissue.

FIG. 3 shows a typical course of the temperature of a lead tip of a defibrillation arrangement in a magnetic resonance tomograph. When the electromagnetic field is switched on (reference numeral 301), the temperature of the lead tip increases abruptly, wherein the steepness of the increase and the maximum temperature are strongly dependent on the position of the lead relative to the electromagnetic field of the magnetic resonance tomograph. When the electromagnetic alternating field is switched off (reference numeral 302), the lead tip cools down relatively quickly due to the relatively low heat capacity thereof.

To solve the above-described heating problem, U.S. patent application publication 2009/0105789 A1 proposes use of a temperature-dependent switch, which disconnects the lead tip from the supply lead if heating occurs. However, such a switch has a distinct hysteresis, the temperature range is difficult to set, and the lead tip can only be switched fully on or off, and therefore, in the switched-off state, it is not possible to stimulate the heart or derive signals.

In addition, U.S. patent application publication 2010/0174348 A1 discloses an implantable electrical lead, the use of which is compatible with an MRI scanner. The lead comprises two parallel resonators which are formed by concentrically coiled insulated lead wires in the interior thereof, and which are tuned to a Larmor frequency of the tissue of a living organism in which the lead will be used. As an additional mechanism for suppressing unwanted influences of the strong electromagnetic field with HF components which exists in an MRI scanner, blocking elements (cable traps) are provided along the lead to prevent currents from being induced in the lead by the HF components. Blocking elements are designed, for example, as interspaced metallic hollow cylinders on the outer circumference of the lead.

BRIEF SUMMARY OF THE INVENTION

An object of one or more embodiments of the invention is to provide an improved device of the type described initially that has improved properties in strong external magnetic fields having alternating field components, and that has a simple design, thereby enabling it to be manufactured at low cost.

This object is provided by a device having the features as claimed herein. Advantageous developments of one or more embodiments of the invention are also claimed herein.

One or more embodiments substantially reduce the influence of strong external fields by providing a galvanic separation in the longitudinal extension of the elongated conductive element of the device. A transformer having a core is provided especially as the separating element, said core being designed such that it can be saturated in a static magnetic field component of the electromagnetic field. The transformer is capacitively decoupled such that high-frequency currents induced in the elongated conductive element by an alternating field component of the electromagnetic field can be mitigated substantially via the transformer.

According to an embodiment of the invention, the saturable core is a ferrite core or a functionally similar core, which is formed of compactly joined, sintered in particular, soft magnetic powder. Possible materials for said core are soft magnetic powders based on Co or Ni, or ceramic powders based on Mn—$ZnO_x$ or Ni—$ZnO_x$ or the like, which are pressed into core shape in particular and may be sintered.

In a first application, the device is a catheter, in particular an ablation, balloon, or insertion catheter, or an electrophysiological catheter.

In an application that is particular important from a current perspective, the device is designed as an electrode lead, wherein the distal end comprises, in particular, an electrode for the stimulation of a heart, an ICD electrode, a transvenous ICD electrode, an electrode for neurostimulation, or an electrode for deep brain stimulation. In that particular case, the transformer is designed to transmit therapy impulses or currents from the proximal end to the distal end.

In another embodiment, the transformer is inserted into the flexible longitudinal extension of the electrode lead. Alternatively, the transformer is inserted into a plug of the electrode lead. In the latter variant, less consideration is given for particularly small dimensions in the structural design of the transformer, although the galvanic separation is placed far away from the distal end of the lead in this case.

In another embodiment of the invention, the transformer is a component of a band filter device disposed in the electrode lead for the selective blanking of high-frequency components of the electromagnetic field. In that particular case, a ferrite core or functionally similar core of the transformer is designed in particular for the automatic adaptation of filter parameters of the filter device to parameters of the electromagnetic field.

Moreover, an electromedical implant is provided which comprises a device of the above-described type, and an impulse-generating device (impulse generator, therapeutic current generator) which contains means for controlling the electrode(s) of the electrode lead. The impulse-generating device comprises detector means for detecting a transformer impedance of the transformer disposed in the electrode lead, and adaptation means connected on the input side to the detector means for adapting the stimulation parameter on the basis of the transformer impedance that was detected.

For use with an above-mentioned electrode lead, in which the transformer is a component of a band filter device, detector means can also be provided for detecting parameters of the external electromagnetic field via the resulting filter parameters of the filter device. In another embodiment, the electrode lead comprises a plurality of cores having different saturation parameters, and the detector means are designed to differentiate between different magnetic field strengths of the electromagnetic field on the basis of the detection of the transformer impedance.

BRIEF DESCRIPTION OF THE DRAWINGS

Further details of one or more embodiments of the invention are described in the following with reference to the figures.

FIGS. 6 and 7A to 7C show further embodiments of a device according to the invention

DETAILED DESCRIPTION OF THE INVENTION

Figure 1:
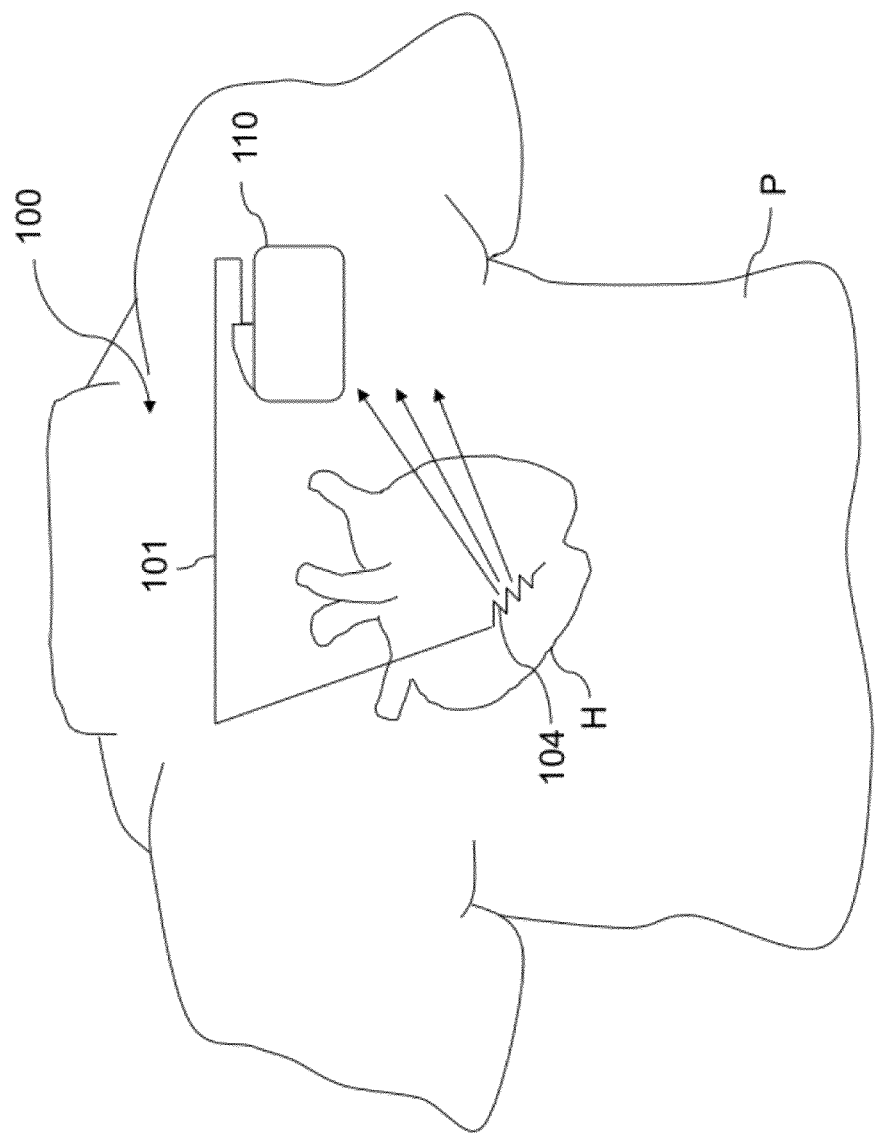
FIG. 1 shows a basic design of an implantable defibrillation arrangement.
Figure 2:
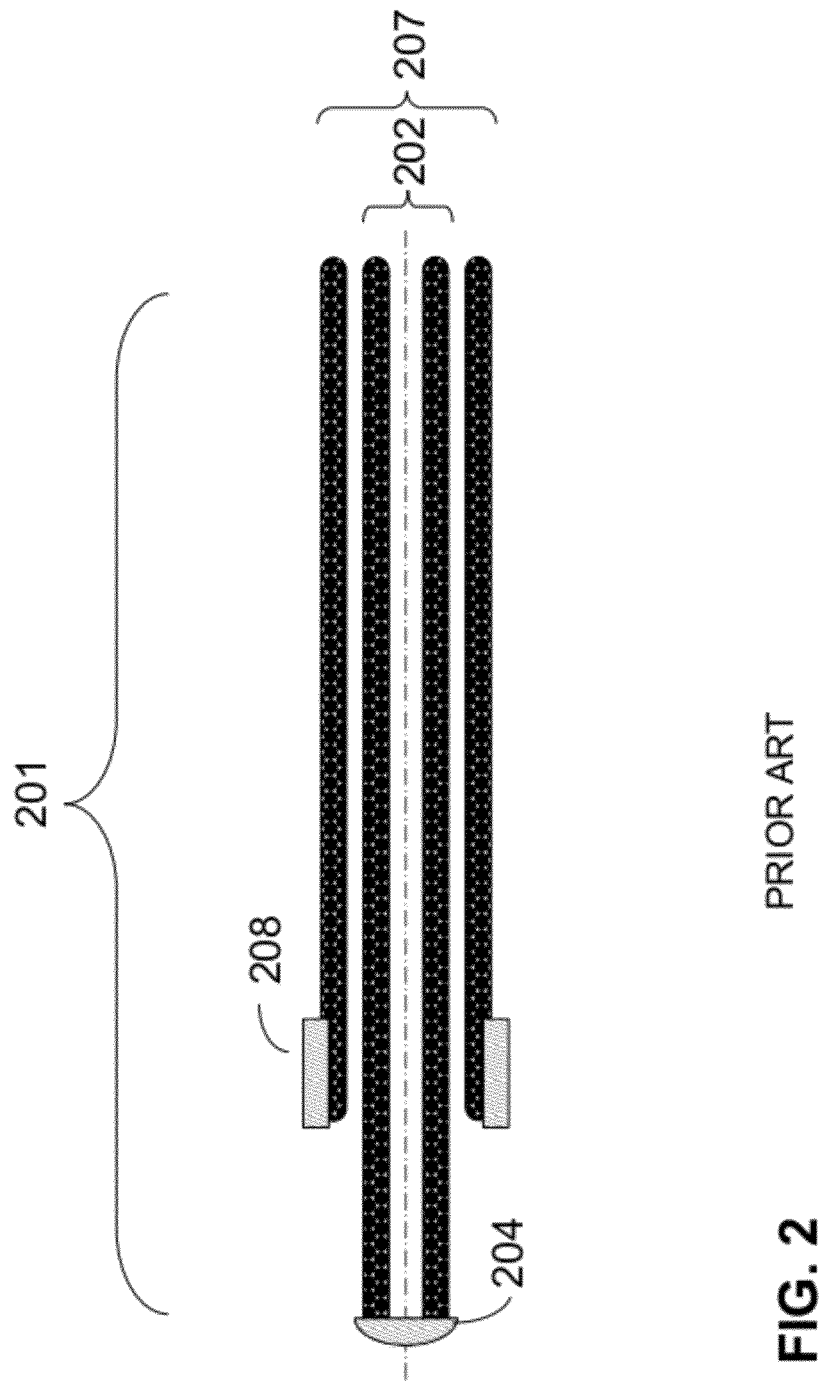
FIG. 2 shows an embodiment of a distal end of an electrode lead.
Figure 3:
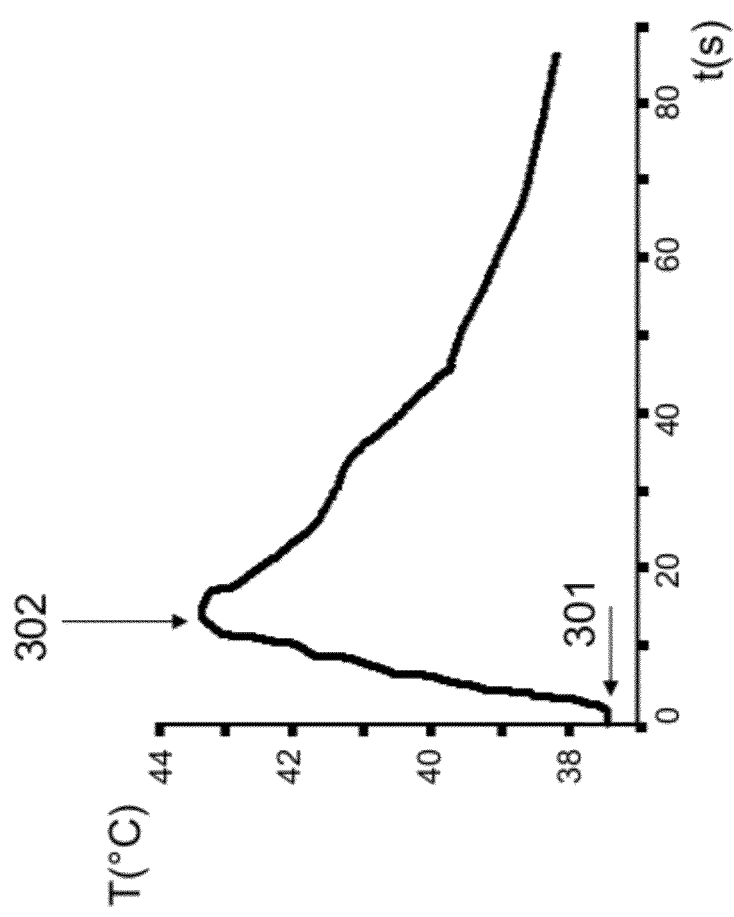
FIG. 3 illustrates a course of temperature of a tip of a lead during coupling of an electromagnetic field using a magnetic resonance tomograph.
Figure 4:
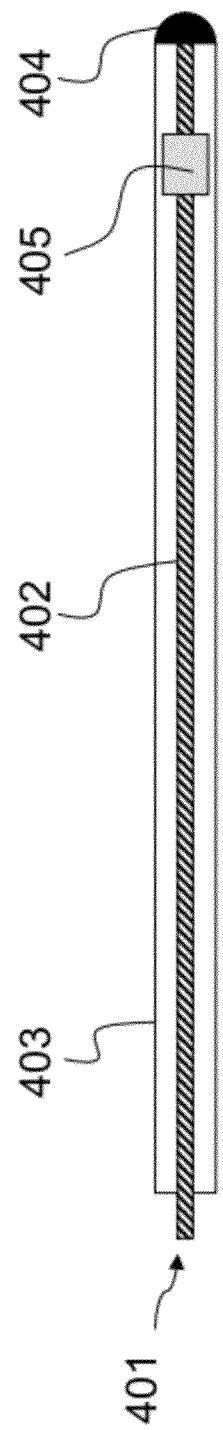
FIG. 4 is a schematic representation of an embodiment of a device according to the invention.

FIG. 4 shows a device 401 according to an embodiment of the invention, which is designed as electrode lead 401. A lead (elongated conductive element) 402 comprises, embedded in an insulating sleeve 403, a distal electrode (tip electrode) 404 and a galvanic separating element 405. The effect of an inductive coupling of a strong external magnetic field with lead 402 is substantially reduced by galvanic separating element 405 in the lead extension, thereby also substantially reducing disadvantageous heating, of tip electrode 404 in particular, which is caused by the currents reduced in the lead. For the rest, separating element 405 is designed such that it is permeable to therapy impulses or currents that are supposed to be transmitted to bodily tissue via electrode lead 401.

Figure 5:
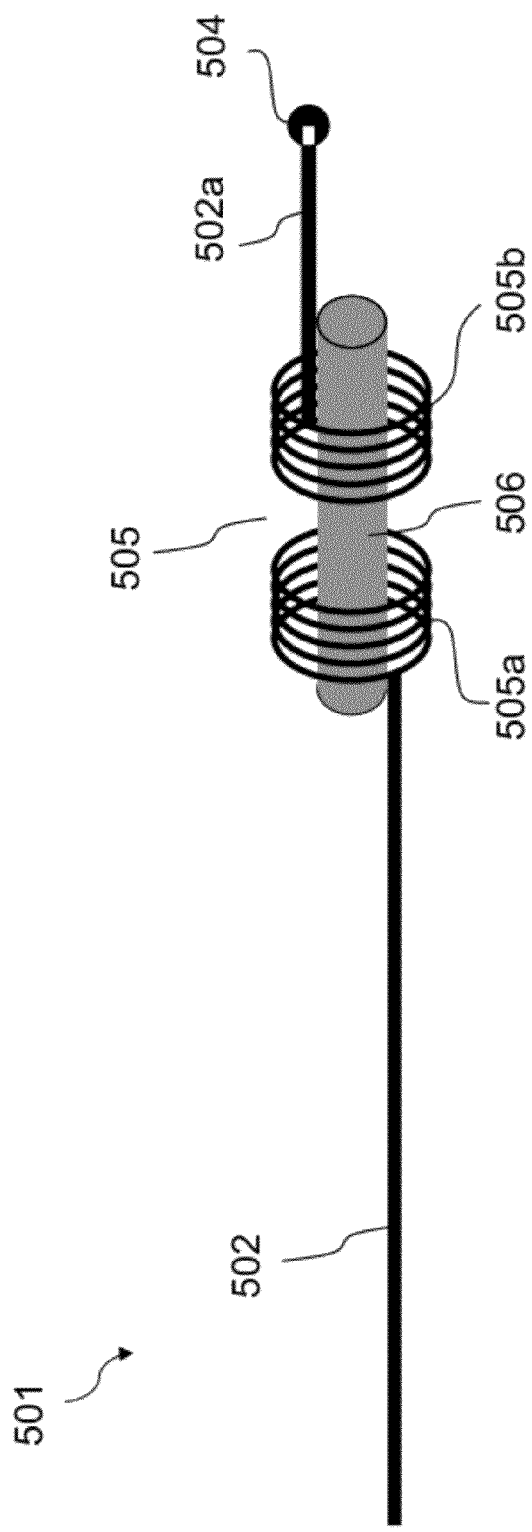
FIG. 5 is a schematic representation of another embodiment of a device according to the invention.

FIG. 5 illustrates another embodiment of a device 501 according to the invention. A first electrode lead (elongated conductive element) 502 comprises a tip electrode 504 on the distal end. In the longitudinal extension of electrode lead 502, close to the distal end, a transformer 505 is provided as a separating element to reduce induction currents coupled into the electrode lead. Transformer 505 comprises a first, proximally disposed coil turn 505a, and a second, distally disposed coil turn 505b on a common core 506 which can be saturated in a static external magnetic field. Distal coil turn 505b is connected to tip electrode 504 via a lead piece 502a.

Transformer 505 creates a galvanic separation of the tip electrode from the larger part of the (insulated) electrode lead 502 which functions as an antenna with respect to an alternating field component of an external electromagnetic field. In such a field, transformer core 506 becomes saturated, and the extreme interferences induced in electrode lead 502 cannot be conducted further to the bodily tissue via the tip electrode, provided the capacitive coupling of the two coil windings 505a and 505b is selected to be adequately low.

The proximal, i.e. antenna-side, coil winding 505a preferably comprises several turns to ensure that the inductance in this (proximal) transformer circuit remains relatively great even when the transformer core is saturated, in order to minimize the "antenna currents". Transformer 505 can therefore be designed as a step-down transformer, for example, on the distal side, which also requires that relative high voltages but relative low currents be conducted via electrode lead 505. Electrode lead 502 can therefore also be designed to be high-resistance, thereby reducing the antenna properties thereof, as the affinity thereof with respect to interference fields. This embodiment is particularly advantageous for electrode leads that are used exclusively for stimulation purposes and do not perform a sensing function, i.e. do not promote signal transmission from the distal end to the proximal end.

FIG. 6 shows a variant of the electrode lead that is depicted in FIG. 5 and is described above. In addition to the configuration shown in FIG. 5, there is a second electrode lead 607 having a corresponding distal lead section 607a and a ring electrode 608 installed thereon. Common transformer 605 also has a decoupling effect with respect thereto, thereby reducing the risk of heating or even local burning of bodily tissue by the electrode, as described above. Hence, coils 505a and 505b may have two or more insulated coils that connect to respect leads on each side of common core 605 for example.

Another particular advantage of this embodiment comprising a transformer is that, in particular, the risk of unwanted stimulation by the gradient fields of the MRT is effectively prevented.

In another embodiment, the inductance L of the coil is tuned to the tissue impedance (to be considered as ohmic resistance R) between electrodes 604 and 608 such that a desired pulse width of the stimulation pulse is obtained, i.e. the time constant tau=L/R has this desired duration.

Figure 7B:
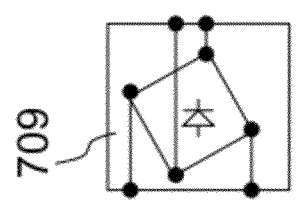
Figure 7C:
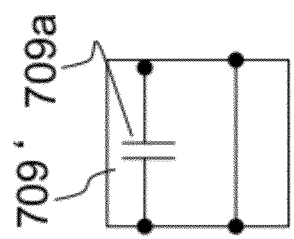

FIGS. 7A to 7C show another variant of the electrode lead depicted in FIG. 6, and in fact one created by adding a signal converter 709. Signal converter 709 is used to convert the alternating voltage signal, which is transmitted via electrode lead 701 for a therapeutic purpose, or an impulse to a signal shape that is more favorable for stimulation. A rectifier circuit can be used for this purpose, as indicated in FIG. 7B. As indicated in FIG. 7C, a modified signal converter 709' can comprise a capacitor 709a, the capacitance C of which is tuned to the inductance of distal coil winding 505b such that the ohmic resistance of lead section 502a, the coil inductance, and the capacitor capacitance form an oscillating circuit with critical damping, i.e. $R=\sqrt{L/C}$.

An alternative embodiment of the invention makes use of the fact that a magnetic coil core becomes saturated at a certain defined field strength, which is accompanied by a reduction in coil inductance. Use is also made of the fact that the HF frequency f of the MRT is bound directly proportionally to the static field strength BO of the MRT via the Larmor relationship.

Figure 8:
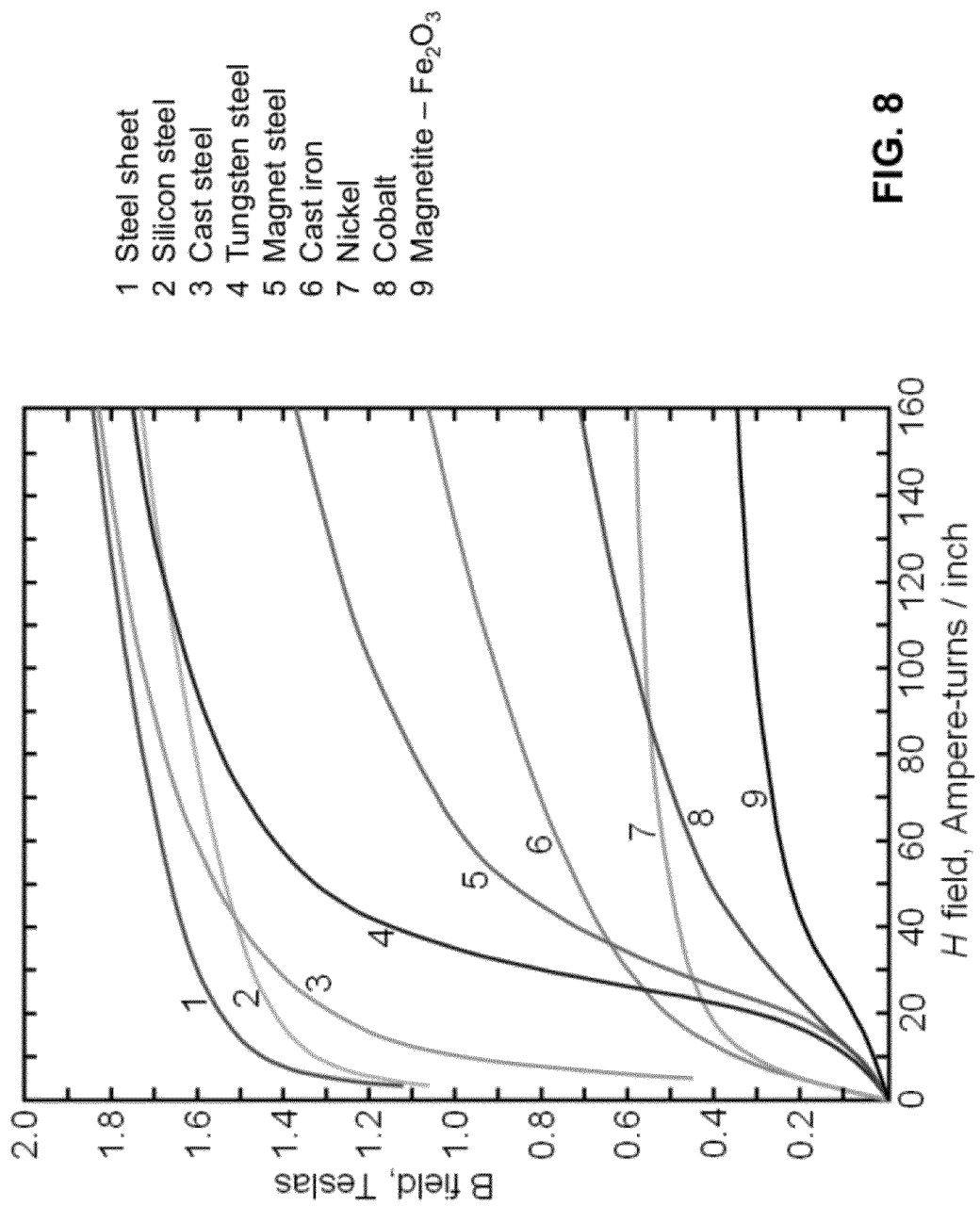
FIG. 8 shows saturation characteristic curves of various core materials for a transformer used in the device according to the invention.

The saturation behavior of various core materials is represented in FIG. 8.

Embodiments may be utilized for the following application cases:

Application case 1: Form series inductance to establish high impedance upstream of the particular electrode pole, by selecting the material of the transformer core such that it does not become saturated in a static magnetic field, where the core is effective and the coil impedance is high, while, in a high static magnetic field, the core is saturated and the inductance of the coil is low. However, if a high-frequency field component is effective in this case, it "compensates" for the relatively low inductance to the extent that the resulting coil impedance still becomes relatively high.

Application case 2: All embodiments of MRI-compatible electrodes/catheters that comprise LC oscillating circuits. If the core becomes saturated here in an external magnetic field with high static field strength, the inductance of the coil winding becomes low and, therefore, the resonance frequency becomes high. The characteristic curve according to which the inductance and, therefore, the frequency change can be adjusted to suit the application via the geometry of the coil and the core, in particular determination of the part of the coil cross section formed by the core.

The same electrode can therefore be made compatible for MRT magnetic field strengths of 1.5 T and 3 T by selecting a core material that saturates between 1.5 T and 3 T (see FIG. 8). Furthermore a plurality of coil having various cores, or various cores in one coil can be used to make the same compatible for 1 T, 1.5 T, and 3 T, for instance. The core materials saturate between 1 and 1.5 T or 1.5 and 3 T.

Figure 9:
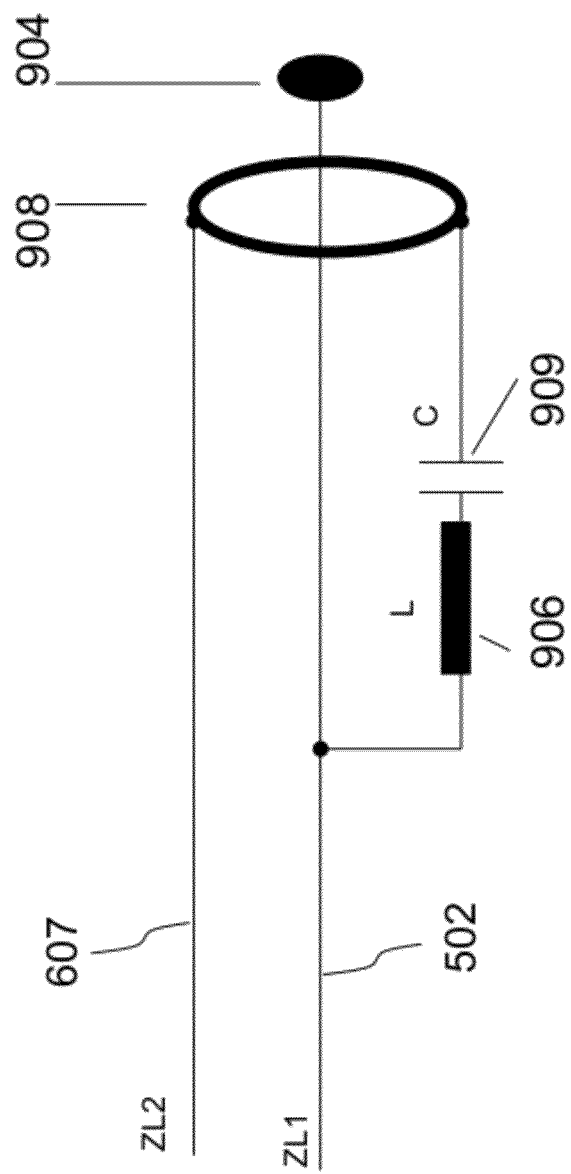
FIG. 9 shows another embodiment of a device according to the invention.

The diversion of the MRT-induced currents to a ring electrode 908 is shown in an equivalent circuit diagram in FIG. 9 (in which reference characters were assigned with reference to the labeling of the components in FIGS. 6 to 7C). The principle is to short circuit tip 904 and ring 908 using the oscillating circuit shown when resonance occurs. 908 can be a therapeutically used ring or a (electrically) floating ring. The advantages compared to other known solutions are the small component sizes, in particular coils having very low inductance, which can therefore be easily incorporated into the electrode design.

The resonance frequency is calculated as follows:

$$f_0 = \frac{1}{2\pi\sqrt{LC}}$$

For a 1.5 T MRT, given a capacitor 909 set to a capacitance C=1 pF, an inductance of "only" approximately 6.5 μH is therefore required in the resonant circuit. Such an arrangement may be installed behind a ring electrode. In order to use this arrangement also in a 3 T-MRT, the inductor L 906 in the resonant circuit is equipped with a core that has a saturation behavior above 1.5 T but below 3 T, and is dimensioned such that the inductance in the resonant circuit at 3 T (saturated core) drops to approximately 1.5 μH, and therefore the resonant frequency is set for a 3 T-MRT. Though the LC series resonant circuit may be advantageous because the impedance at resonance is less than the impedance of a capacitor alone, embodiments having a capacitor alone that connects a conductor of the lead to a ring (or a pole with other shape like an ICD shock coil) is in keeping with the spirit of the invention.

Also possible is the use of a transformer instead of inductor L 906 in the above described configuration.

Similar or functionally identical configurations such as those described above can also be used with alternative devices for filtering the MRT-induced HF currents.

Suitable core materials, in which saturation occurs between 1.5 T and 3 T, are composed mainly of cobalt-iron containing 47-50% cobalt. Silicon-iron comprising 3-4% silicon is also suitable.

Embodiments of the invention are not limited to the above-described examples and emphasized aspects, but rather are possible in a large number of modifications that lie within the scope of handling by a person skilled in the art.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A device for medical applications, comprising
an elongated conductive element having
   a proximal end;
   a distal end;
   wherein said distal end comprises at least one distal tip electrode;
   a separating element configured to galvanically separate the proximal end from the distal end;
   wherein said separating element is configured to be located in a region between said distal end and said proximal end;
   wherein said region is configured to increase in temperature through absorption of energy from an electromagnetic field by said separating element;
   wherein the separating element is a transformer, wherein said transformer comprises a transformer core configured to be saturated in a static magnetic field component of the electromagnetic field;
   wherein said transformer is configured to create a galvanic separation of said at least one distal tip electrode from other regions of said elongated conductive element; and
   wherein the transformer is capacitively decoupled such that high-frequency currents induced in the elongated conductive element by an alternating field component of the electromagnetic field are substantially mitigated via the transformer.

2. The device according to claim 1, wherein the transformer core is a saturable core comprising a ferrite core or a functionally similar core, which comprises compactly joined, sintered or soft magnetic powder.

3. The device according to claim 1, wherein said transformer core comprises a plurality of saturable cores having different saturation parameters, and a saturation characteristic curve having different slopes.

4. The device according to claim 1, wherein said elongated conductive element is configured to be coupled with a catheter, or an ablation, balloon, or insertion catheter, or electrophysiological catheter.

5. The device according to claim 1, wherein said elongated conductive element is an electrode lead;
   wherein said electrode lead comprises a flexible longitudinal extension and a plug, wherein said flexible longitudinal extension is located between said proximal end and said distal end, closer to said distal end than said proximal end;

wherein said distal tip electrode is configured to stimulate a heart, and wherein said at least one distal tip electrode comprises an ICD electrode, a transvenous ICD electrode, an electrode for neurostimulation, or an electrode for deep brain stimulation, and wherein said transformer is configured to transmit therapy impulses or currents from the proximal end to the distal end of the electrode lead.

6. The device according to claim 5, wherein said region comprises said flexible longitudinal section of the electrode lead, and wherein the transformer is located in the flexible longitudinal extension of the electrode lead.

7. The device according to claim 5, wherein said region comprises said plug of the electrode lead, and wherein the transformer is located in said plug of the electrode lead.

8. The device according to claim 5, further comprising a band filter device and wherein the transformer is a component of said band filter device and wherein said band filter device is disposed in the electrode lead and configured to selectively blank high-frequency components of the electromagnetic field.

9. The device according to claim 8, wherein the transformer core is a saturable core comprising a ferrite core or a functionally similar core, which comprises compactly joined, sintered or soft magnetic powder and wherein said ferrite core or said functionally similar core of the transformer is configured to automatically adapt filter parameters of the band filter device to parameters of the electromagnetic field.

10. An electromedical implant comprising a device according to claim 5, further comprising
an impulse-generating device configured to control the electrode of the electrode lead on based on a stimulation parameter, wherein the impulse-generating device comprises
a detector configured to detect a transformer impedance of the transformer disposed in the electrode lead, and
an adapter connected on an input side to the detector wherein said adapter is configured to adapt the stimulation parameter on based on the transformer impedance detected by said detector.

11. The implant according to claim 10, wherein said transformer core comprises a plurality of cores having different saturation parameters, and wherein the detector is configured to differentiate between different magnetic field strengths of the electromagnetic field on based on detection of the transformer impedance by said detector.

12. The implant according to claim 1, wherein said transformer core is a common core that comprises a plurality of windings on each side of said transformer core that are respectfully coupled to a plurality of corresponding electrodes at said distal end of said at least one distal tip electrode.

13. A device for medical applications, comprising
an elongated conductive element comprising an electrode lead, wherein said electrode lead includes
a proximal end;
a distal end;
wherein said distal end comprises at least one distal tip electrode;
a separating element configured to galvanically separate the proximal end from the distal end;
wherein said separating element is configured to be located in a region between said distal end and said proximal end;

wherein said region is configured to increase in temperature through absorption of energy from an electromagnetic field by said separating element;

wherein the separating element is a transformer, wherein said transformer comprises a transformer core configured to be saturated in a static magnetic field component of the electromagnetic field;

wherein said transformer is configured to create a galvanic separation of said at least one distal tip electrode from other regions of said elongated conductive element;

wherein the transformer is capacitively decoupled such that high-frequency currents induced in the elongated conductive element by an alternating field component of the electromagnetic field are substantially mitigated via the transformer;

wherein said electrode lead comprises a flexible longitudinal extension and a plug;

wherein said flexible longitudinal extension is located between said proximal end and said distal end, closer to said distal end than said proximal end;

wherein said distal tip electrode is configured to stimulate a heart, and wherein said at least one distal tip electrode comprises an ICD electrode, a transvenous ICD electrode, an electrode for neurostimulation, or an electrode for deep brain stimulation; and wherein said transformer is configured to transmit therapy impulses or currents from the proximal end to the distal end of the electrode lead.

14. The implant according to claim 13, further comprising an impulse-generating device configured to control the electrode of the electrode lead on based on a stimulation parameter, wherein the impulse-generating device comprises
a detector configured to detect a transformer impedance of the transformer disposed in the electrode lead, and
an adapter connected on an input side to the detector wherein said adapter is configured to adapt the stimulation parameter on based on the transformer impedance detected by said detector.

15. The implant according to claim 14, wherein said transformer core comprises a plurality of cores having different saturation parameters, and wherein the detector is configured to differentiate between different magnetic field strengths of the electromagnetic field on based on detection of the transformer impedance by said detector.

16. A device for medical applications, comprising
an elongated conductive element comprising an electrode lead, wherein said electrode lead comprises
a proximal end;
a distal end;
wherein said distal end comprises at least one distal tip electrode; a separating element configured to galvanically separate the proximal end from the distal end;
wherein said separating element is configured to be located in a region between said distal end and said proximal end;
wherein said region is configured to increase in temperature through absorption of energy from an electromagnetic field by said separating element;
wherein the separating element is a transformer, wherein said transformer comprises a transformer core configured to be saturated in a static magnetic field component of the electromagnetic field;

wherein said transformer is configured to create a galvanic separation of said at least one distal tip electrode from other regions of said elongated conductive element;

wherein the transformer is capacitively decoupled such that high-frequency currents induced in the elongated conductive element by an alternating field component of the electromagnetic field are substantially mitigated via the transformer;

wherein said electrode lead comprises a flexible longitudinal extension and a plug;

wherein said flexible longitudinal extension is located between said proximal end and said distal end, closer to said distal end than said proximal end;

wherein said distal tip electrode is configured to stimulate a heart, and wherein said at least one distal tip electrode comprises an ICD electrode, a transvenous ICD electrode, an electrode for neurostimulation, or an electrode for deep brain stimulation;

wherein said transformer is configured to transmit therapy impulses or currents from the proximal end to the distal end of the electrode lead;

an impulse-generating device configured to control the electrode of the electrode lead on based on a stimulation parameter, wherein the impulse-generating device comprises a detector configured to detect a transformer impedance of the transformer disposed in the electrode lead, and an adapter connected on an input side to the detector wherein said adapter is configured to adapt the stimulation parameter on based on the transformer impedance detected by said detector; and wherein said transformer core comprises a plurality of cores having different saturation parameters, and wherein the detector is configured to differentiate between different magnetic field strengths of the electromagnetic field on based on detection of the transformer impedance by said detector.

* * * * *